(12) United States Patent
Hansmann et al.

(10) Patent No.: US 11,679,216 B2
(45) Date of Patent: Jun. 20, 2023

(54) PROCESS FOR OPERATING A VENTILATOR AND VENTILATOR OPERATING ACCORDING TO THE PROCESS

(71) Applicant: DRÄGERWERK AG & CO. KGAA, Lübeck (DE)

(72) Inventors: Hans-Ullrich Hansmann, Barnitz (DE); Karsten Hiltawsky, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1278 days.

(21) Appl. No.: 16/135,374

(22) Filed: Sep. 19, 2018

(65) Prior Publication Data
US 2019/0083726 A1 Mar. 21, 2019

(30) Foreign Application Priority Data
Sep. 20, 2017 (DE) ...................... 10 2017 008 791.1

(51) Int. Cl.
*A61M 16/00* (2006.01)
*A61B 5/087* (2006.01)
*A61B 5/091* (2006.01)
*A61M 16/01* (2006.01)
(Continued)

(52) U.S. Cl.
CPC .......... *A61M 16/024* (2017.08); *A61B 5/087* (2013.01); *A61B 5/091* (2013.01); *A61M 16/0003* (2014.02); *A61M 16/0009* (2014.02); *A61M 16/01* (2013.01); *A61M 16/0066* (2013.01); *A61M 16/0081* (2014.02); *A61M 16/20* (2013.01); *A61M 16/205* (2014.02); *A61M 2016/0027* (2013.01); *A61M 2016/0036* (2013.01); *A61M 2205/50* (2013.01); *A61M 2230/46* (2013.01); *G16H 20/40* (2018.01)

(58) Field of Classification Search
CPC ............ A61M 16/024; A61M 16/0003; A61M 16/0009; A61M 16/01; A61M 16/0081; A61M 16/205; A61M 16/0066; A61M 16/20; A61M 2016/0027; A61M 2016/0036; A61M 2205/50; A61M 2230/46; A61B 5/087; A61B 5/091; G16H 20/40
See application file for complete search history.

(56) References Cited

U.S. PATENT DOCUMENTS

| 5,915,381 A | 6/1999 | Nord |
| 2002/0026941 A1 | 3/2002 | Biondi et al. |

(Continued)

FOREIGN PATENT DOCUMENTS

| DE | 80 15 055 U1 | 1/1985 |
| DE | 10 2004 019 122 A1 | 11/2005 |

(Continued)

*Primary Examiner* — Steven O Douglas
(74) *Attorney, Agent, or Firm* — McGlew and Tuttle, P.C.

(57) ABSTRACT

A process for operating a ventilator (12) and a ventilator (12) operating according to the process are provided. A pressure target value ($p_z$) is determined during a phase of exhalation (48) as a function of a compliance (C) determined in relation to the lungs (14) of a patient being ventilated by means of the ventilator (12).

11 Claims, 7 Drawing Sheets

(51) Int. Cl.
   *G16H 20/40*    (2018.01)
   *A61M 16/20*    (2006.01)

(56)         References Cited

U.S. PATENT DOCUMENTS

| | | | |
|---|---|---|---|
| 2003/0168066 A1* | 9/2003 | Sallvin | A61M 16/00 |
| | | | 128/204.21 |
| 2010/0236555 A1* | 9/2010 | Jafari | A61M 16/0666 |
| | | | 128/204.23 |
| 2012/0216811 A1* | 8/2012 | Kimm | G16H 40/63 |
| | | | 128/204.23 |
| 2013/0167843 A1 | 7/2013 | Kimm et al. | |
| 2014/0123979 A1* | 5/2014 | Doyle | A61M 16/0875 |
| | | | 128/204.23 |
| 2018/0015244 A1* | 1/2018 | Isaza | A61M 16/0833 |
| 2018/0110957 A1 | 4/2018 | Hansmann et al. | |
| 2019/0388634 A1* | 12/2019 | Enk | A61M 16/024 |
| 2020/0038611 A1* | 2/2020 | Isaza | A61M 16/026 |
| 2020/0108215 A1* | 4/2020 | Nakai | A61B 5/087 |

FOREIGN PATENT DOCUMENTS

| | | |
|---|---|---|
| DE | 10 2016 206 442 A1 | 10/2017 |
| DE | 10 2016 012 824 A1 | 4/2018 |
| WO | 2017148639 A1 | 9/2017 |

* cited by examiner

--Prior Art--

PROCESS FOR OPERATING A VENTILATOR AND VENTILATOR OPERATING ACCORDING TO THE PROCESS

CROSS REFERENCE TO RELATED APPLICATIONS

This application claims the benefit of priority under 35 U.S.C. § 119 of German Application 10 2017 008 791.1, filed Sep. 20, 2017, the entire contents of which are incorporated herein by reference.

TECHNICAL FIELD

The present invention pertains to a process for operating a ventilator (also known as a respirator), especially a ventilator in the form of a combined anesthesia device and ventilator, as well as to such a device operating according to the process.

BACKGROUND

A ventilator or a ventilator in the form of a combined anesthesia device and ventilator—hereinafter summarily called ventilator—acts, in a manner known per se, as a breathing gas delivery unit, for example, by the ventilator comprises a gas delivery unit comprising a connection interface to an external gas supply or comprising a ventilator breathing gas delivery unit, for example, in the form of a pump, especially of a pump in the form of a piston-and-cylinder unit or a so-called bag-in-bottle unit, a fan impeller or the like (also referred to as a compressor). Likewise in a manner known per se, the pressure is raised on the side of the ventilator to a value above the alveolar pressure, i.e., the pressure within the patient's lungs, by means of the ventilator during the inhalation. This pressure difference leads to a volume flow in the direction of the patient's lungs. When pressure equalization is achieved, the volume flow disappears. The process is reversed during exhalation and the pressure on the side of the ventilator is reduced compared to the alveolar pressure, so that a volume flow from the patient's lungs occurs until a pressure equalization is achieved here as well.

A pressure control, a volume control and various mixed forms with different limitations are known for such an operation. For example, processes in which the inspiratory overpressure is increased by the pressure drop in an endotracheal tube inserted into the trachea are known under the keyword Automatic Tube Compensation (ATC): $\Delta p = (R_{endotracheal} + R_{ventilation}) *$ volume flow. The inspiratory overpressure is then obtained with the flow resistance of the endotracheal tube ($R_{endotracheal}$) and the flow resistance of the ventilation tube between the ventilator and the endotracheal tube ($R_{ventilation}$).

Small valve units, which make possible a pressure measurement and a measurement of the volume flow very close to the patient, as well as very small valves, which make it possible to control and regulate the airway pressure ($P_{AW}$) during inhalation and exhalation, are known from the older German patent application 10 2016 009 836.8, which was not previously published.

However, it is not yet quite optimal when known standard values are used for the flow resistances $R_{endotracheal}$ and $R_{ventilation}$. COPD patients, i.e., patients who have chronic obstructive pulmonary disease (COPD) and consequently greatly restricted airways—with a correspondingly high flow resistance—as well as rigid, nonelastic lungs—with a correspondingly low so-called pulmonary stiffness (compliance)—are therefore ventilated with special ventilation modes (flow constancy, volume control, pressure limitation, etc.).

The exhalation valve, which regulates to a desired positive end-expiratory pressure (PEEP; positive end-expiratory pressure), is available for the exhalation. However, this is based on the pressure measured on the device side. The alveolar or intrinsic PEEP is higher by the value of the pressure drop over the entire exhalation branch. The residual volume may tend to increase steadily especially in COPD patients due to the increased exhalation resistance.

In addition, the work of the respiratory muscles needed for the breathing (in addition to the breathing gas delivery unit) leads to an increased $CO_2$ production, and the resulting $CO_2$ is eliminated only insufficiently because of the difficult gas exchange.

SUMMARY OF THE INVENTION

Based on this, one object of the present invention is to provide a process for controlling the ventilation parameters, in which the alveolar pressure corresponds to the predefined values as accurately as possible and allows optimized ventilation in the sense of a high gas exchange in relation to the alveolar pressure fluctuation.

This object is accomplished by means of a process for operating a ventilator wherein a pressure target value is determined during a phase of exhalation as a function of a compliance determined in relation to the lungs of a patient being ventilated by means of the ventilator. Provisions are made for this in a process for operating a ventilator for the determined pressure target value $p_z$.

The process and embodiments of the process which will be described below and the process steps comprised thereby are carried out automatically, i.e., without a special intervention on the part of the operator of the respective ventilator. The automatic performance of the process steps takes place under the control of a control unit of the ventilator. This control unit comprises a processing unit comprising a microprocessor (or one or more processors) as well as a memory. A control program executable by the processor unit, which program is executed during the operation of the ventilator by the processing unit thereof, is or can be loaded into the memory. Operating actions of the operator in connection with the process are limited, for example, to the predefining of parameters. The above-mentioned object is thus also accomplished by means of a control unit for controlling a ventilator, which control unit operates according to the process as here and hereinafter described and comprises means for carrying out the process for this. The present invention is preferably implemented in software. The present invention is thus also a computer program with program code instructions executable by a computer, namely, the control unit of the ventilator, on the one hand, and a storage medium with such a computer program, i.e., a computer program product with program code means, on the other hand, as well as finally also a control unit or a ventilator, into the memory of which control unit or ventilator such a computer program is or can be loaded as a means for carrying out the process and embodiments thereof.

An exemplary embodiment of the present invention will be explained in more detail below on the basis of the drawings. Mutually corresponding objects or elements are provided with the same reference numbers in the figures.

The exemplary embodiment should not be considered to be a limitation of the present invention. Additions and modifications, especially those that the person skilled in the art can find, for example, by combining or modifying individual features or process steps described in the general or special part of the description as well as contained in the claims and/or the drawings with a view to accomplishing the object and lead to a new object or to new process steps or sequences of process steps through combinable features.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
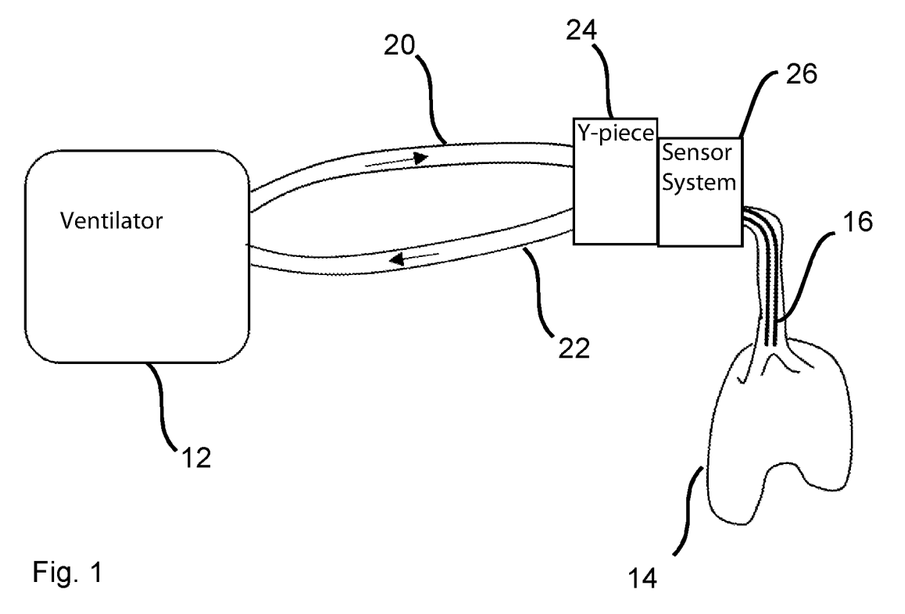
FIG. 1 is a schematic view showing a ventilator for ventilating a patient connected to the ventilator.

Referring to the drawings, in a highly simplified form, the view in FIG. 1 schematically shows a ventilator 12 on the left-hand side and the lungs 14 of a patient on the right-hand side. The patient is connected to the ventilator 12 by an endotracheal tube 16, hereinafter called tube 16 for short, being inserted into his lungs 14, and by a ventilation tube 18 (FIG. 2) with an inhalation branch 20 and with an exhalation branch 22 extending between the ventilator 12, on the one hand, and the tube 16, on the other hand. The inhalation branch 20 and the exhalation branch 22 of the ventilation tube 18 are brought together by means of a Y-piece 24 in front of the tube in a manner that is known per se. For example, the volume flow (dV/dt) of the breathing gas flowing into the patient's lungs 14 and/or of the breathing gas (exhaled gas) flowing out of the patient's lungs 14 is measured between the Y-piece 24 and the tube 16, i.e., close to the patient, by means of a sensor system 26.

Figure 2:
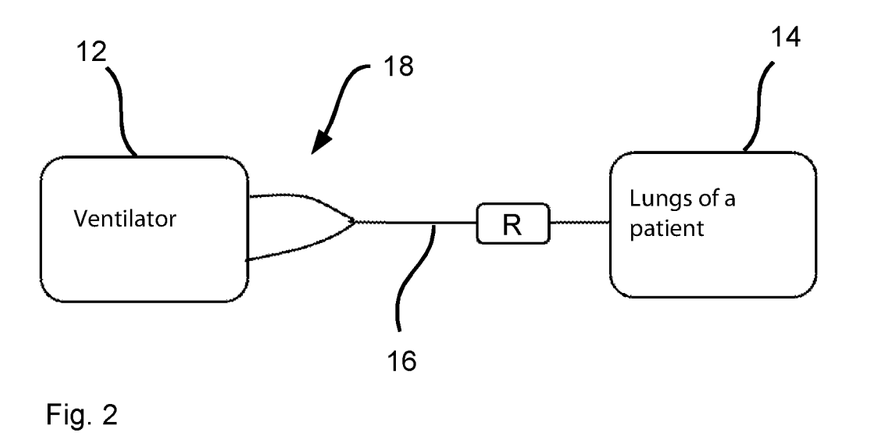
FIG. 2 is a schematic view showing a ventilator for ventilating a patient connected to the ventilator.

The view in FIG. 2 shows the conditions according to FIG. 1 in an even more simplified form. The view is limited to the ventilator 12 and the patient's lungs 14, on the one hand, as well as to the ventilation tube 18 as well as—in extension of the ventilation tube 18—to the tube 16. The entirety of the ventilation tube 18 and tube 16 is characterized by their respective flow resistance R.

Figure 3:
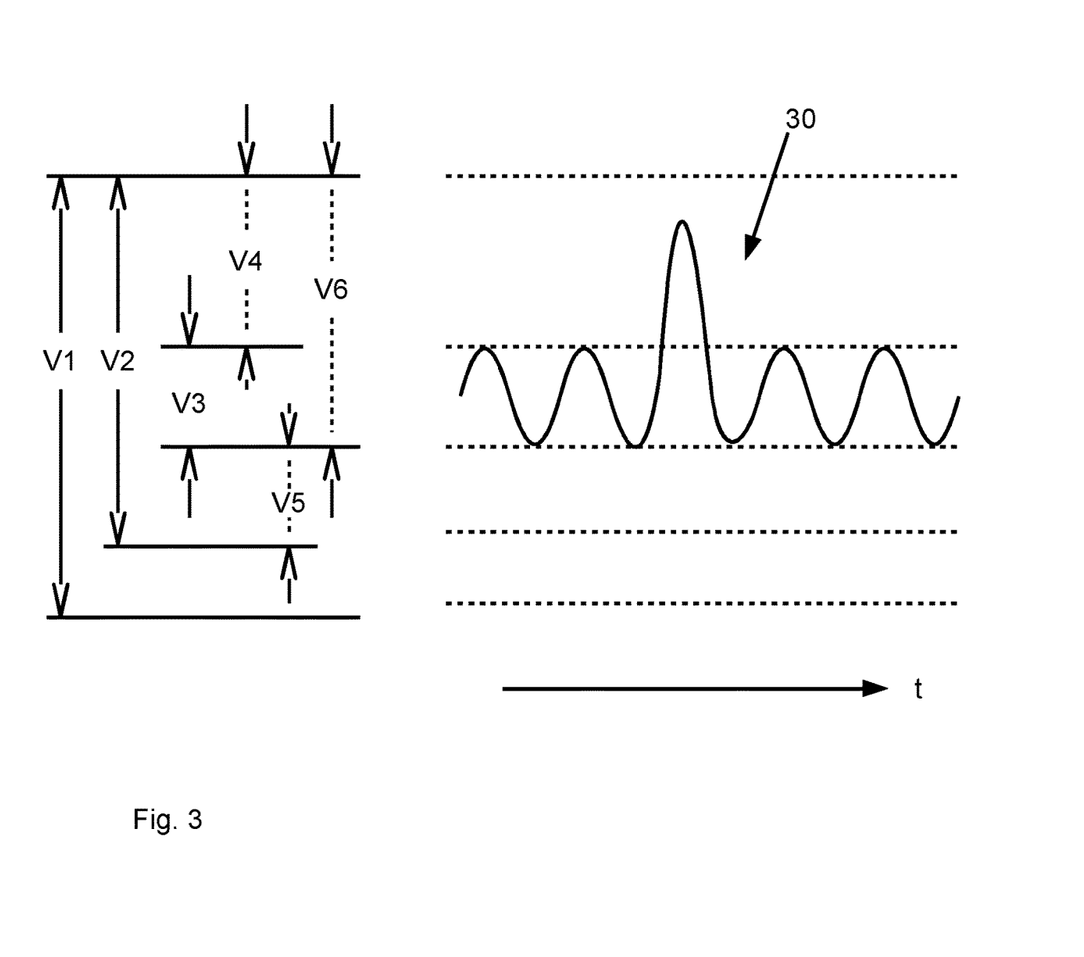
FIG. 3 is a diagram showing different volumes relevant during the ventilation of a patient.

The view in FIG. 3 shows in a simplified form a volume curve 30 during the breathing over the time t and the volumes involved, namely, a total capacity V1 of the respective lung 14, a so-called vital capacity V2, which comprises a tidal volume V3 as well as an inspiratory reserve volume V4 and an expiratory reserve volume V5. Breathing takes place in the range of the tidal volume V3 during normal, spontaneous breathing and also during ventilation by means of a ventilator 12. If more breathing gas volume is to be administered per breath during a ventilation, the operation is changed over into the range of the inspiratory reserve volume V4. The sum of the tidal volume V3 and the inspiratory reserve volume V4 determines the inspiratory capacity V6 of the lungs 14.

Figure 4:
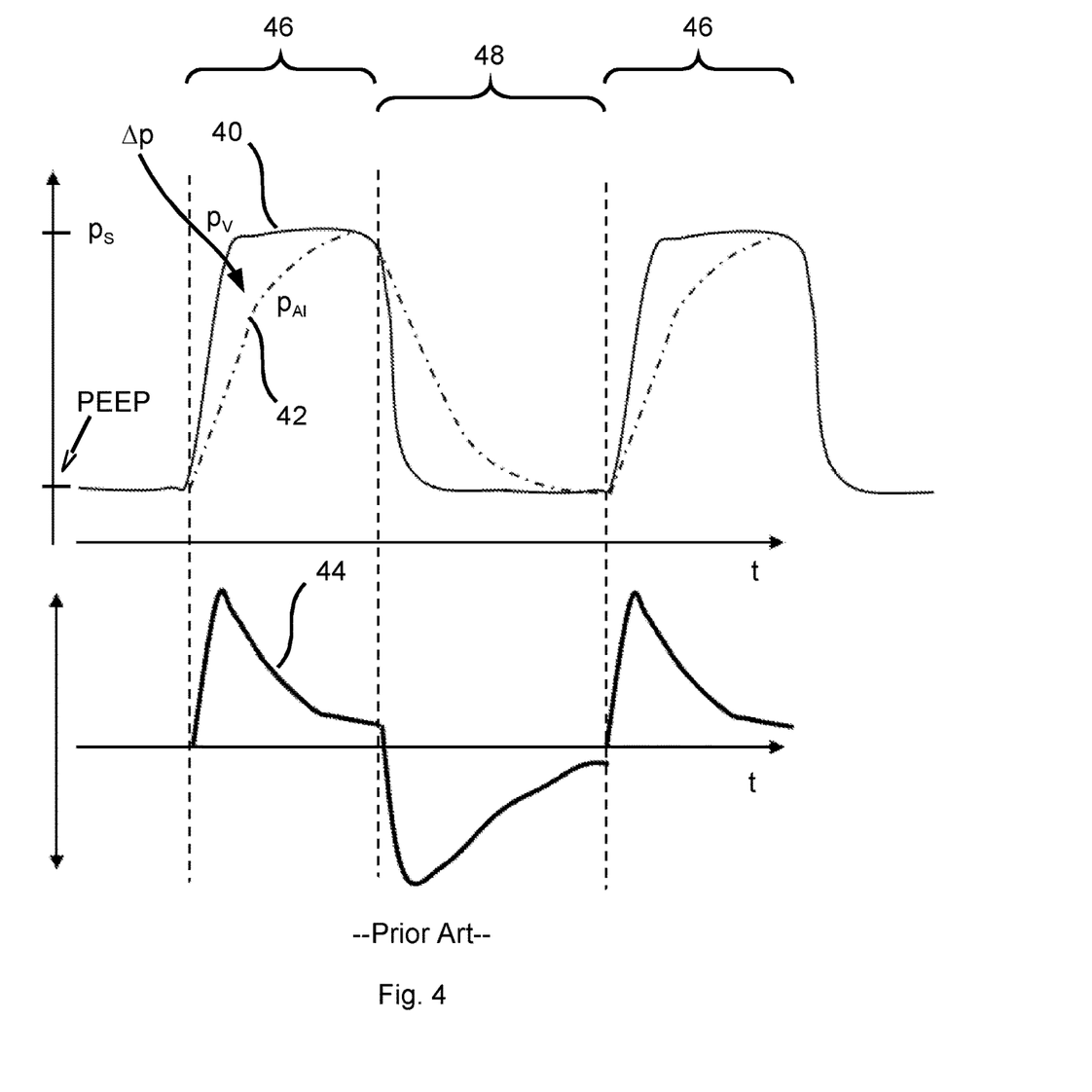
FIG. 4 is a device-side pressure curve and a lung-side pressure curve as well as a corresponding volume flow during a conventional ventilation.

The view in FIG. 4 shows—always over the time t—a first pressure curve and a second pressure curve, 40, 42, in the upper area, as well as a curve 44 of the volume flow dV/dt belonging to the first and second pressure curves 40, 42. Phases of inhalation 46 and phases of exhalation 48 are defined by means of vertical lines.

The first pressure curve 40 is the curve showing a pressure ($p_v$) measured at the ventilator 12 over time. The first pressure curve 40 is obtained on the basis of a control or regulation of the ventilator 12, which control or regulation is known per se. The first pressure curve 40 fluctuates, as intended, between a respective predefined or predefinable PEEP (positive end-expiratory pressure) and a set point ($p_s$) for the pressure during the phase of inhalation 46.

The second pressure curve 42 results from the first pressure curve 40 and is the curve showing an alveolar pressure ($p_m$) measured as close to the patient as possible over time. For distinction, the first pressure curve 40 is called the device-side pressure curve 40 and the second pressure curve 42 is called the alveolar pressure curve or lung-side pressure curve 42. The area between the alveolar pressure curve 42 and the device-side pressure curve 40 is proportional to a product of the flow resistance R (flow resistance of the ventilation tube 18 and the tube 16) by the respective volume flow dV/dt: $\Delta p = R*dV/dt$.

Figure 5:
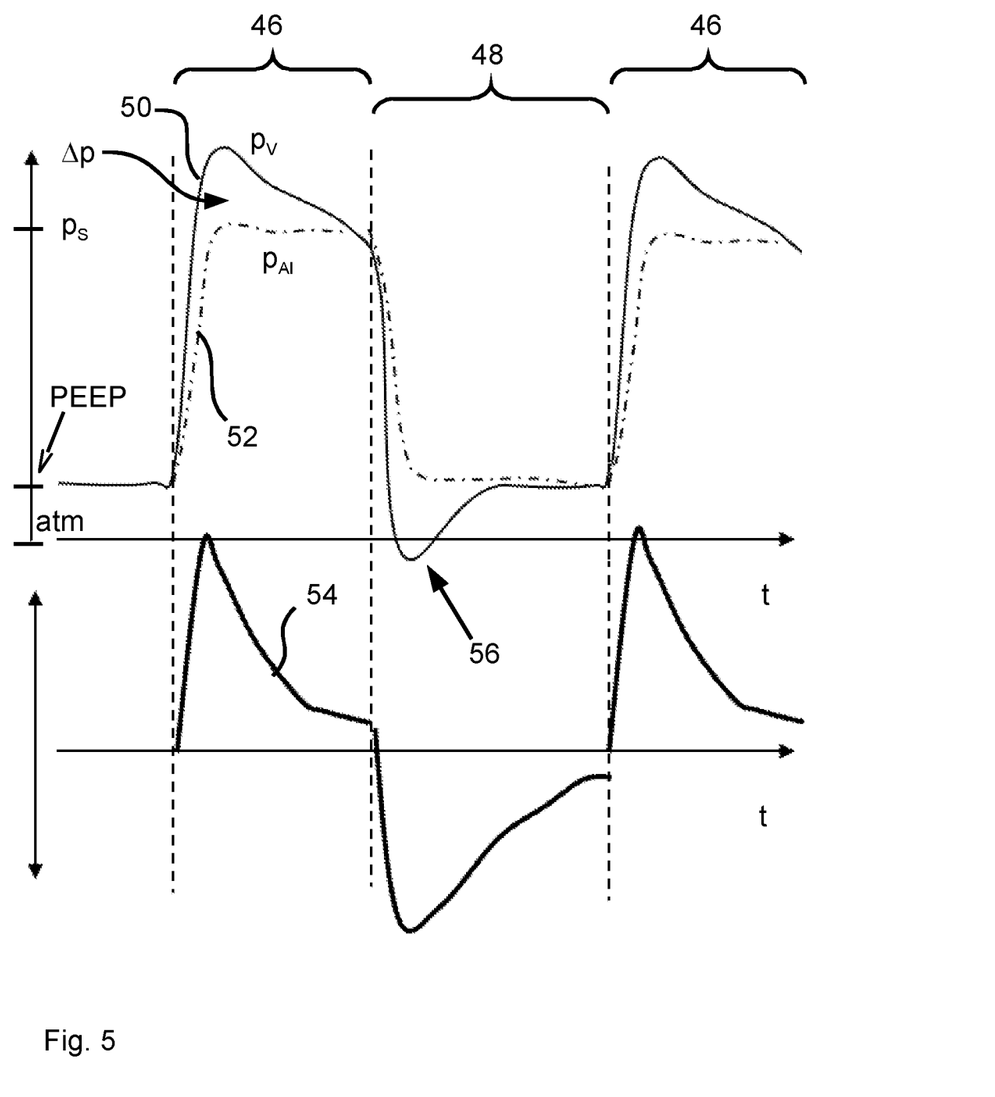
FIG. 5 is a device-side pressure curve and a lung-side pressure curve as well as a corresponding volume flow during a ventilation corresponding to the solution according to the invention.

The view in FIG. 5 shows compared to this—likewise over the time t—a pressure curve 50, 52 adapted according to the solution according to the invention, namely, an adapted device-side pressure curve 50 as well as a resulting, adapted alveolar pressure curve 52. As can be seen, the adapted device-side pressure curve 50 has changed against the device-side pressure curve 40 in FIG. 4 at the beginning of the phase of inhalation 46 because a higher maximum is reached there above the set point ($p_s$). The adapted device-side pressure curve 50 approaches the device-side pressure curve 40 shown in FIG. 4 at the end of the phase of inhalation 46. A change can also be seen at the beginning of the phase of exhalation 48 in the adapted device-side pressure curve 50 compared to the device-side pressure curve 40 in FIG. 4. The values of the device-side pressure curve 40 according to FIG. 4 are undershot here beyond the PEEP and even drop below the ambient pressure (vacuum range 56) designated by "atm" in the view in the situation shown in FIG. 5. The adapted device-side pressure curve 50 again approaches the device-side pressure curve 40 according to FIG. 4 at the end of the phase of exhalation. The adapted device-side pressure curve 50 is not shown in FIG. 5 any longer for the subsequent phase of inhalation 46. In fact, the adapted device-side pressure curve 50 usually continues over a plurality of phases of inhalation and exhalation 46, 48.

An adapted alveolar pressure curve 52 as well as an adapted volume flow curve 54 result from the adapted device-side pressure curve 50. The alveolar pressure curve 52 remains above the PEEP during the entire exhalation 48 despite the device-side vacuum 56 at the beginning of the phase of exhalation 48.

As can be seen, the adapted alveolar pressure curve 52 essentially corresponds to the device-side pressure curve 40 according to FIG. 4. The rise of the alveolar pressure curve 42, which can be seen in the situation shown in FIG. 4 and is slowed down compared to the device-side pressure curve 40, is compensated or at least essentially compensated. The resulting adapted alveolar pressure curve 52 with comparatively steep flanks at the beginning and at the end of the phase of inhalation and phase of exhalation 46, 48 as well as with a uniform or essentially uniform plateau during the individual phases of inhalation and exhalation 46, 48 corresponds to what was hitherto (FIG. 4) predefined on the device side, but has become established alveolarly only in a distorted or delayed form because of the flow resistance R.

It is consequently possible to compensate the flow resistance R by calculation by increasing (or excessively increasing) the pressure generated or made available by means of the ventilator 12 on the device side in the manner shown in FIG. 4 at the beginning of each phase of inhalation 46 and additionally reducing it at the beginning of each phase of exhalation 48.

The peculiarity of the solution being proposed here is that the alveolar pressure curve 52 corresponds or essentially corresponds to the values predefined on the device side not only during the phase of inhalation 46, but this was also achieved for the phase of exhalation 48. The ventilator 12 is controlled or regulated during ventilator operation in a manner that guarantees the described adapted device-side pressure curve 50. Instead of the set point $p_s$, a pressure target value $p_z$ ($p_z=p_s+R*dV/dt$) formed with the set point $p_s$ is used for this during a phase of inhalation 46, and a pressure target value $p_z$ ($p_z=PEEP-R*dV/dt$) is used instead of the PEEP during a phase of exhalation 48. This corresponds basically to a variable change in the set point $p_s$ during a phase of inhalation 46 as well as to a variable change in PEEP during a phase of exhalation 48, since the term $R*dV/dt$ is time-dependent based on the volume flow flowing in. Depending on the value resulting for the term $R*dV/dt$, the pressure target value $p_z$ ($p_z=PEEP-R*dV/dt$) may also become negative for the phase of exhalation 48, so that a pressure target value $p_z$ below the ambient pressure ($p_z<atm$) will be obtained. To generate a device-side pressure with a negative pressure target value $p_z$, the ventilator 12 has a vacuum port 28 (FIG. 7) and is connected to a pressure sink in this way.

Depending on the pressure target value $p_z$ determined during the exhalation, the ventilator 12 makes available a vacuum relative to the alveolar pressure as needed and at least temporarily by means of a control or regulation. This may be brought about by means of an exhalation valve opening to the ambient pressure, as this is described in DE 10 2016 012 824.0 (corresponding to U.S. 2018110957 (A1), which is incorporated by reference in its entirety), which will be mentioned below with additional details. As an alternative or in addition, this may be brought about by means of a control or regulation of the vacuum port 28. The ventilator 12 optionally makes available a vacuum in relation to the ambient pressure (vacuum range 56) by means of the vacuum port 28. In any case, an increased pressure difference (between the device-side pressure and the alveolar pressure) may be used for the exhalation 48 as a drive for the volume flow from the patient's lungs 14. It should be noted that the range of the expiratory reserve volume V5 is not reached or at least it is not reached in an uncontrolled manner. The inspiratory capacity V6 of the patient's lungs 14 is otherwise undershot, so that the risk of collapse of individual regions of the lungs does, in principle, increase. To eliminate this risk, the so-called compliance of the lungs 14, i.e., the elasticity of the lungs, is determined and monitored during the phase of exhalation.

Figure 6:
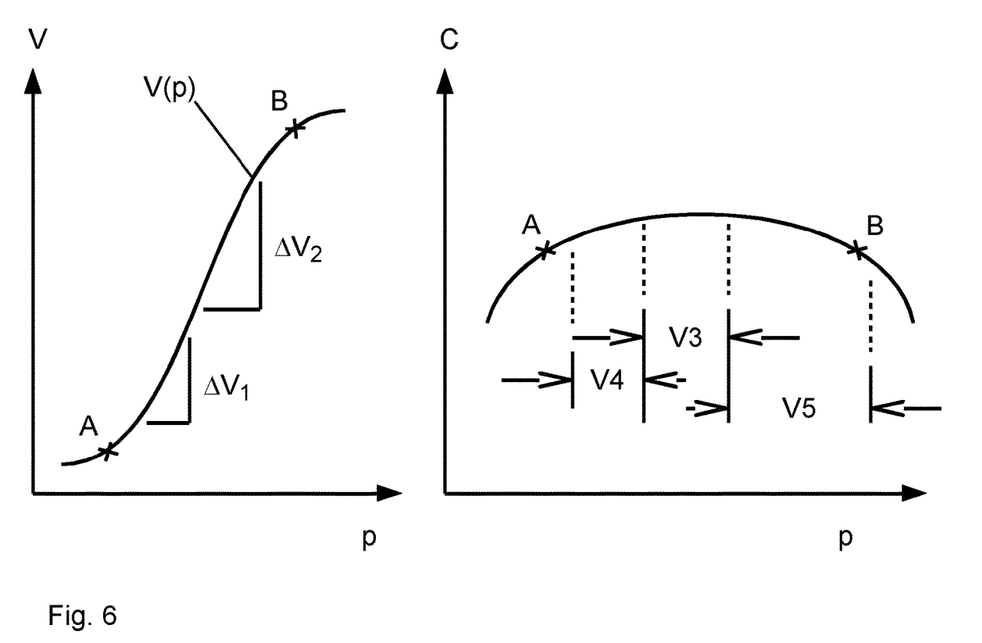
FIG. 6 is a diagram showing a pressure volume curve and a compliance pressure curve explaining the compliance of the lungs of a patient.

FIG. 6 shows for this, on the left side, a view of the compliance C as a gradient in a pressure-volume diagram. The data of the pressure-volume diagram is acquired at the start of ventilation with a test (compliance) maneuver involving a pressure volume loop with increasing and decreasing pressure to provide the relationship of the volume to the pressure. This may be e.g., increasing the pressure slightly from 5 mbar to 7 mbar over time to provide a compliance starting value. This test (compliance) maneuver may be repeated at times during subsequent ventilation, such that the compliance value may be updated. Depending on the clinical picture of the patient, an increase of pressure and decrease of pressure, for determining the pressure volume curve, could be continuously applied slightly from 3 mbar to 5 mbar, or from 5 mbar to 7 mbar or in another suitable way, depending on the individual condition of the patient. Instead of a continuous increase and decrease could proceed by discrete steps, for example with a step size of 0.2 mbar. FIG. 6 illustrates that depending of the prefilling of the respective volume and hence depending on the already existing expansion of an envelope enclosing the volume, different volumes ($\Delta V1$, $\Delta V2$) can be fed in order to bring about an equal pressure increase. So-called inflection points are designated by A and B. The compliance C is obtained as a function of the pressure p and the volume V, as this is shown in FIG. 6 in a simplified manner on the right-hand side, by deriving the curve shown in the left-hand part of the pressure-volume diagram, namely forming the first derivative of V(p), namely $C=dV(p)/dp$. The compliance C remains essentially equal over the tidal volume V3 (cf. FIG. 3). The compliance C changes markedly over the expiratory reserve volume V5. In addition, one of the inflection points (inflection point B) is exceeded at the edge of the expiratory reserve volume V5. Exceeding an inflection point should, however, be avoided. The inspiratory reserve volume V4 of the lungs 14 adjoins the tidal volume V3 on the left-hand side.

For the operation of the ventilator 12, this means that a vacuum can be applied on the device side during the phase of exhalation 48, especially at the beginning of the phase of exhalation 48, as long as the expansion of the patient's lungs 14 does not become too low. The expansion of the patient's lungs 14 may also become lower in this case—at least briefly—than in the relaxed state.

Excessively minimal expansion of the patient's lungs 14 is ruled out whenever the product of the particular measured (sensor system 26) volume flow by the flow resistance R determined based on measurements (sensor system 26) is greater than the vacuum applied on the device side. A higher vacuum may be applied on the device side only if it is ensured by frequent measurements of the compliance C and of the corresponding volume that the expiratory reserve volume V5 is not reached.

The measurement of the compliance C may be carried out, for example, according to the principle described in the older German patent application not published previously referenced (DE 10 2016 012 824.0) entitled "Process and Device for the Adaptive Regulation of a Positive End-expiratory Pressure (PEEP)," and corresponding U.S. 2018110957 (A1) whose contents shall be considered to have been fully included in the description being presented here, also for the purpose of including features from U.S. 2018110957 (A1) in claims for defining the invention underlying the description being presented here.

According to DE 10 2016 012 824.0 and corresponding U.S. 2018110957 (A1), the pressure present on the device side (FIG. 4: Pressure curve 40; FIG. 5: Pressure curve 50) is briefly reduced within a pressure reduction period during a phase of exhalation 48. The duration of the pressure reduction period is very short compared to the overall duration of the phase of exhalation 48 and may be, for example, in a range of 10 msec to 30 msec. Based on the short-term reduction of the pressure present on the device side, there will be a (brief) increase in the volume flow. The pressure present on the device side corresponds to a product of the flow resistance by the resulting volume flow. The volume flow during the phase of exhalation 48 is the volume flow of the exhaled breathing gas (exhaled gas flow) and the flow resistance is correspondingly the exhalation resistance $R_{exp}$. Consequently, the particular exhalation resistance $R_{exp}$ can be determined on the basis of the pressure present on the device side as well as the resulting volume flow at different points of the tidal volume of the patient's lungs 14, i.e., for different states of expansion of the patient's lungs 14. Based on the same brief increase in the pressure present on the device side—contrary to the previous brief pressure reduction—a (brief) reduction of the exhaled gas flow will occur. The compliance C of the patient's lungs 14 can be calculated based on the resulting rise of the curve of the exhaled gas flow, on the one hand, as well as on the value of the pressure reduction, on the other hand. Depending on the time of the brief pressure increase, the compliance C of the patient's lungs 14 can also be determined at different points from their tidal volume.

According to the principle being disclosed here, the determined compliance C is a certain factor for a controlled application of an adapted pressure target value $p_z$ ($p_z$=PEEP−X; X=$R_{exp}$*dV/dt) during the phase of exhalation 48. Provisions are made for this for the term X, which lowers the pressure target value $p_z$ possibly to below the PEEP and possibly even to below the ambient pressure, to depend on the particular determined compliance C of the patient's lungs: X=f(C).

Figure 7:
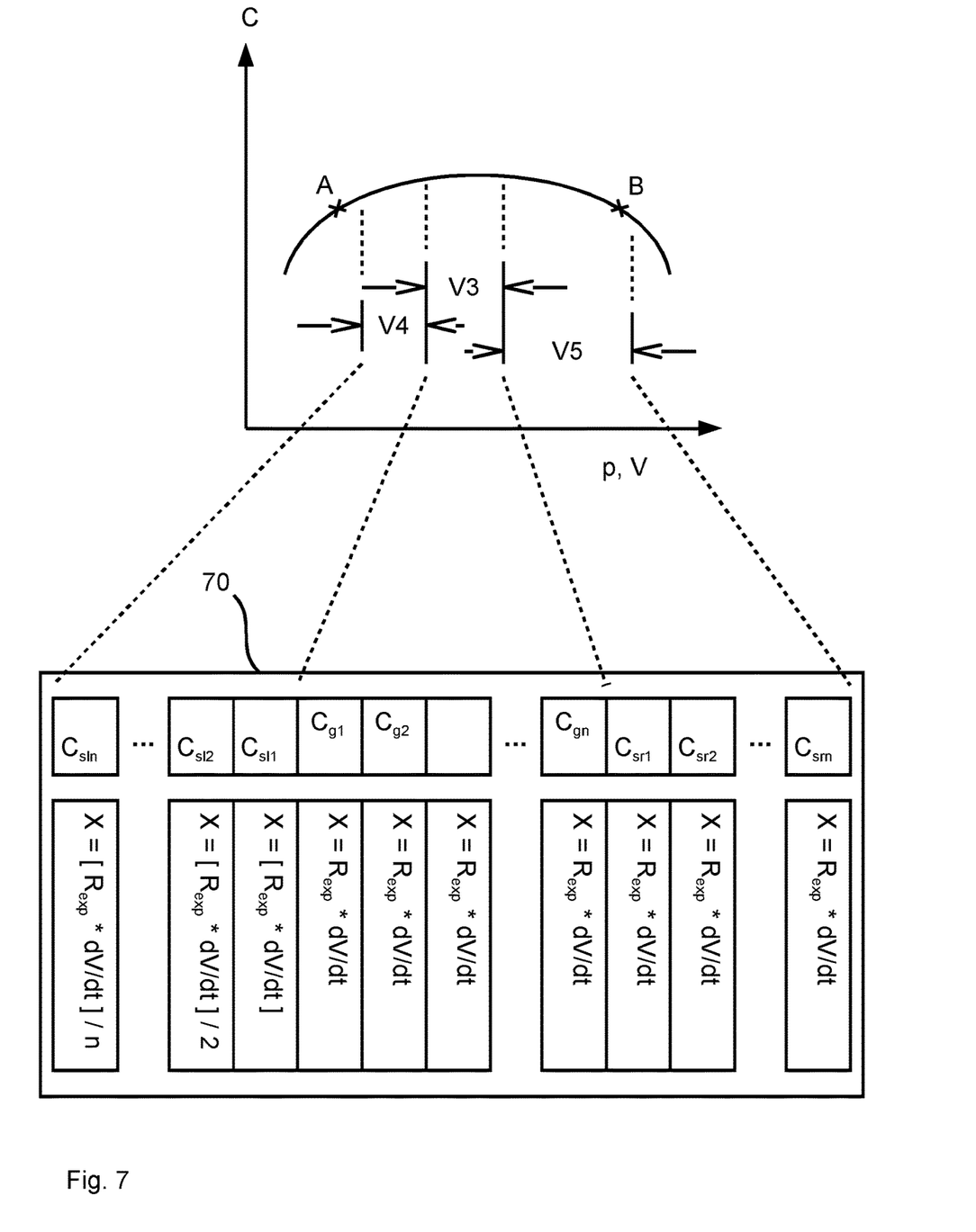
FIG. 7 is a diagram illustrating a lookup table for a possibility of a compliance-dependent determination of a pressure target value $p_z$ during a phase of exhalation.

It is considered for this, for example, that the value of the term X is obtained according to the contents of a lookup table 70, as this is shown in a schematically simplified manner in the view shown in FIG. 7. The view in FIG. 7 shows the dependence of the contents of the lookup table 70 on the particular determined compliance C of the patient's lungs 14 due to the view of the compliance C being taken over from the preceding FIG. 6. As long as the value determined for the instantaneous compliance C is in the range of the tidal volume V3, the compliance values are "good" compliance values (subscript "g" for "good"). If the value determined for the instantaneous compliance C is outside this range, the compliance values are correspondingly "poor" compliance values (subscript "s" for "poor;" "sl:" poor on the left side, "sr:" poor on the right side).

Accordingly, values for a "good" compliance C are filed, for example, in such a lookup table 70 ($C_{g1}$, $C_{g2}$, . . . , $C_{gn}$), and the lookup table 70 shows the term $R_{exp}$*dV/dt for each corresponding compliance value in case of a "good" compliance C. In case of a "poor" compliance, i.e., at compliance values outside the "good" range, for example, the last value used for X is reduced, and the "poorer" the compliance value is, i.e., the farther the compliance value is from the edge of the "good" range, the more greatly is it optionally reduced. This is shown in the view in FIG. 7 for the range to the left of the "good" compliance (range V4), where n represents the distance from the edge of the "good" range. For example, a case differentiation is possible as an alternative to such a lookup table 70, so that the value for X is obtained, for example, as follows:

| | |
|---|---|
| X = $R_{exp}$ * dV/dt | \| $C_{gl}$ < C < $C_{gn}$ |
| X = n [$R_{exp}$ * dV/dt] | \| C > $C_{gn}$; n = 1 |
| X = [$R_{exp}$ * dV/dt]/n | \| C < $C_{gl}$; n = 1, 2, 3, 4 . . . |

It was formulated above that a vacuum exceeding the product of the measured volume flow by the resistance R (exhalation resistance $R_{exp}$) may only be applied on the device side if it is ensured by frequent measurement of the compliance C and of the corresponding volume that the expiratory reserve volume V5 is not reached. It is even possible theoretically to utilize a part of the expiratory reserve volume V5. This requires a continuous (slight) vacuum relative to the ambient pressure during the terminal phase of the exhalation 48.

Figure 8:
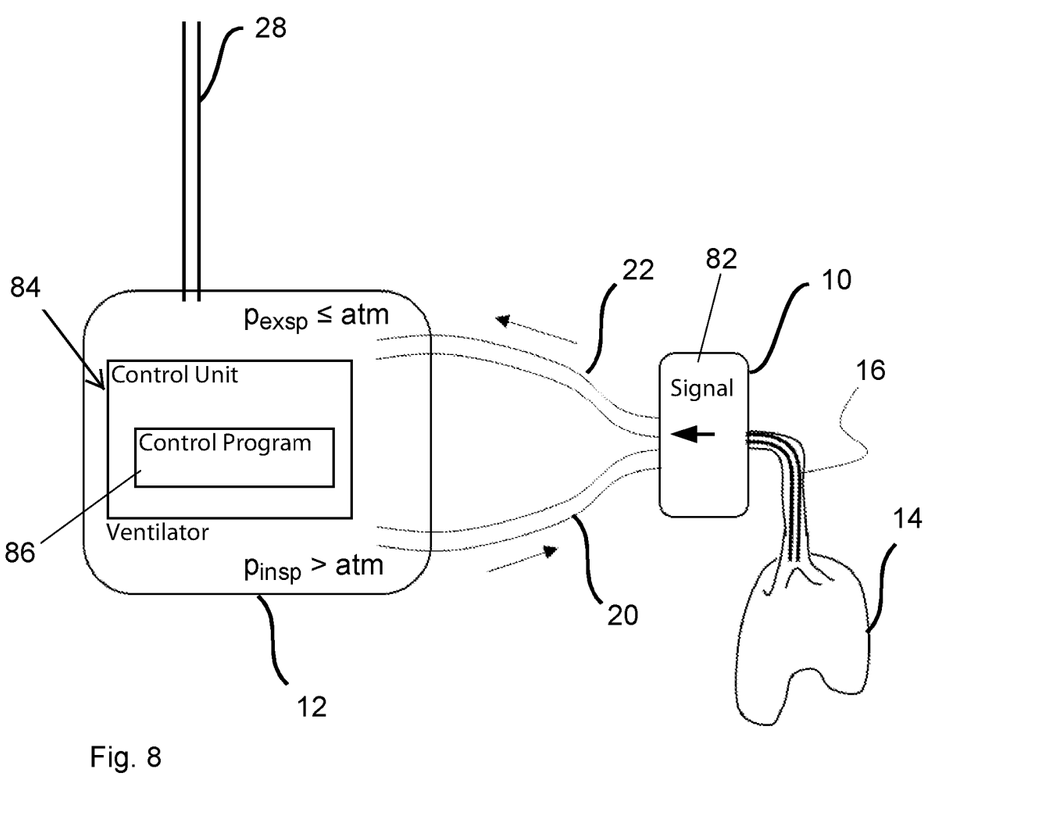
FIG. 8 is a schematic view showing a ventilator as shown in FIG. 1 or FIG. 2 with means for carrying out solution according to the invention.

Finally, the view in FIG. 8 shows the ventilator (ventilator module) 12 and a patient module 10. The ventilator (ventilator module) 12 is an optionally multipart unit. The ventilator module 12 comprises electrical and/or pneumatic interfaces and comprises a gas delivery unit comprising a connection interface to an external gas supply or comprising a ventilator breathing gas delivery unit, for example, in the form of a pump, especially of a pump in the form of a piston-and-cylinder unit or a so-called bag-in-bottle unit, a fan impeller or the like (also referred to as a blower or a compressor). The pneumatic interfaces include a vacuum port 28, and a connected inhalation module (inspiratory connections) leading to the inhalation branch 20 and a connected exhalation module (expiratory connections) leading to exhalation branch 22. The patient module 10 acts as a user interface of the ventilator 12 and comprises either a breathing mask or the like or—as is shown—a tube 16, or it can be connected to a breathing mask or the like or to a tube 16. The patient module 10 is correspondingly arranged close to the patient. The patient module 10 comprises, furthermore, the sensor system 26 (FIG. 1), namely, the sensor system 26 at least for pressure measurement and for volume flow measurement, or such a sensor system 26 is arranged outside the patient module 10, but close to the patient module 10. Based on the arrangement of the patient module 10 close to the patient, the pressure measurement and the volume flow measurement are thus also carried out close to the patient, so that losses due to the distance (and of the resulting resistance) between the ventilator 12 and the patient do not have a disturbing effect on the measurement in the previously experienced manner.

An inhalation pressure $p_{insp}$, which is especially constant and is predefined or can be predefined by the user, is made available by the ventilator 12 for the ventilation of the patient for the inhalation, and an exhalation pressure $p_{exsp}$, which is especially constant and is likewise predefined or can be predefined by the user, is made available for the exhalation. The inhalation pressure $p_{insp}$ is above the ambient pressure (atm), and a volume flow into the patient's lungs 14 ("pushing") results from the inhalation pressure $p_{insp}$. A volume flow out of the patient's lungs 14 ("suction") results from the exhalation pressure $p_{exsp}$.

Either an exhalation valve (not shown here; see DE 10 2016 012 824.0 and FIG. 1 in that document) is provided at the patient module 10 for this suctioning operation, or the ventilator 12 comprises the vacuum port 28 on the exhalation branch 22 or in a continuation of the exhalation branch 22. Such an exhalation valve opens to the ambient pressure (atm) and thus ensures the pressure difference necessary for the exhalation between the alveolar pressure, which is high following the preceding inhalation, and the ambient pressure. In case of a vacuum port 28, the exhalation valve is located in the exhalation branch 22, especially within the patient module 10 in the exhalation branch 22. To obtain the desired pressure target value $p_z$, the exhalation valve is actuated with a control signal intended for influencing the position of the exhalation valve.

The exhalation valve is actuated on the basis of at least one signal 82 from the sensor system 26. The at least one signal 82 may be a measured value (for example, a measured value for the volume flow) recorded by means of the patient module 10 or a plurality of measured values. The processing of the signal 82 may take place in the patient module 10 or in the ventilator 12. For processing in the ventilator 12, the signal 82 is transmitted to the ventilator and to a control unit 84 located there in a wired or wireless manner in a manner known, in principle, per se. The control unit 84 assumes the processing of the at least one signal 82 and determines, for example, the compliance C, the exhalation resistance $R_{exp}$, the pressure target value $p_z$ as well as a control signal for the exhalation valve. The control unit 84 comprises a processing unit in the form of a microprocessor, or one or more processors or the like as well as a memory, into which a computer program executable by means of the processing unit and which acts as a control program 86 is loaded. A control signal determined by a control unit 84 in the ventilator 12 for the exhalation valve and/or the pressure target value is transmitted by the control unit 84 to the patient module 10 and it is active there for the actuation of the exhalation valve. As an alternative, the processing of the at least one signal 82 may also be carried out by means of the patient module 10 itself. The patient module 10 now comprises a control unit 84, as it is shown in the view shown in FIG. 8 as a part of the ventilator 12. Such a control unit 84 likewise determines the pressure target value $p_z$ and/or a control signal 88 for the exhalation valve. This valve can then be actuated directly. The actuation of an inhalation valve takes place correspondingly for the control of the pressure conditions in the inhalation branch 20.

The patient module 10 may be configured, in principle, in the manner as described in US 20130167843 (which is incorporated by reference in its entirety).

The control program 86 comprises an implementation of the steps explained above for determining the pressure target value $p_z$ in software, and the execution of the control program 86 during the operation of the ventilator 12 accordingly brings about the compliance-dependent determination of the pressure target value $p_z$ and further the automatic, compliance-dependent setting of the pressure target value $p_z$.

Individual aspects of the description being submitted here, which are in the foreground, can be summarized as follows: Proposed is a process for operating a ventilator 12 and a ventilator 12 operating according to the process, in which a pressure target value $p_z$ is determined during a phase of exhalation 48 as a function of a compliance C determined in relation to the lungs 14 of a patient being ventilated by means of the ventilator 12.

While specific embodiments of the invention have been shown and described in detail to illustrate the application of the principles of the invention, it will be understood that the invention may be embodied otherwise without departing from such principles.

APPENDIX

List of Reference Designations

10 Patient module
12 Ventilator
14 Lungs, patient's lungs
16 Tube, endotracheal tube
18 Ventilation tube
20 Inhalation branch
22 Exhalation branch
24 Y-piece
26 Sensor system
28 Vacuum port
30 Volume curve, device-side pressure curve
40 First pressure curve, device-side pressure curve
42 Second pressure curve, alveolar pressure curve
44 Volume flow curve
46 Phase of inhalation
48 Phase of exhalation
50 Adapted device-side pressure curve
52 Adapted alveolar pressure curve
54 Adapted volume flow curve
56 Vacuum range
70 Lookup table
80 Vacuum port valve
82 Signal
84 Control unit
86 Control program
88 Control signal
V1 Total capacity of the lungs
V2 Vital capacity of the lungs
V3 Tidal volume
V4 Inspiratory reserve volume of the lungs
V5 Expiratory reserve volume of the lungs
V6 Inspiratory capacity of the lungs

What is claimed is:

1. A process for operating a ventilator, the process comprising the steps of:
   ventilating a patient with the ventilator;
   determining a compliance in relation to the lungs of a patient being ventilated with the ventilator via a control unit based on input from a sensor system; and
   determining a pressure target value during a phase of exhalation as a function of the determined compliance via the control unit.

2. A process in accordance with claim 1, wherein the compliance is determined based on measured values recorded during operation of the ventilator by means of a sensor system arranged at a spaced location from the ventilator and close to the patient.

3. A process in accordance with claim 1, wherein the pressure target value is increased or reduced stepwise during a phase of exhalation when the determined compliance is outside a predefined or predefinable range of compliance values.

4. A process in accordance with claim 1, wherein the pressure target value is reduced at least at times to below an ambient pressure prevailing in an area of the ventilator.

5. A process according to claim 1, wherein a control program comprising program code executes, by means of the control unit of the ventilator, the steps of determining a compliance and determining a pressure target value.

6. A ventilator comprising:

a ventilator module comprising a breathing gas delivery unit, an inhalation branch connection and an exhalation branch connection;

a sensor system; and a control unit configured to:

determine a compliance in relation to the lungs of a patient being ventilated with the ventilator based on input from the sensor system; and determine a pressure target value during a phase of exhalation as a function of the determined compliance.

7. A ventilator in accordance with claim 6, further comprising a patient module, which can be placed close to the patient, the patient module being signal connected to the ventilator module for the purpose of signal transmission and fluid connected to the ventilator module for admitting inhalation gas to detect an inhalation pressure, the patient module comprising sensors and being configured to determine measured values for determining the compliance of the lungs of the patient being ventilated by means of the ventilator.

8. A ventilator in accordance with claim 6, further comprising an exhalation valve, which is arranged close to the patient and can be actuated to obtain the pressure target value during a phase of exhalation.

9. A ventilator in accordance with claim 6, wherein:

the ventilator module further comprises a vacuum port and a vacuum port valve associated with the vacuum port; and the vacuum port valve can be actuated to obtain the pressure target value during a phase of exhalation.

10. A ventilator in accordance with claim 6, wherein the control unit control unit comprises a processing unit and a memory, and wherein a control program is loaded into the memory to determine the compliance and to determine the pressure target value.

11. A patient module of a ventilator comprising a ventilator comprising a breathing gas delivery unit, an inhalation branch connection and an exhalation branch connection, a sensor system; and a control unit configured to determine a compliance in relation to the lungs of a patient being ventilated with the ventilator based on input from the sensor system and to determine a pressure target value during a phase of exhalation as a function of the determined compliance, the patient module comprising:

signal connections to the ventilator module for the purpose of signal transmission;

fluid connections to the ventilator module for admitting inhalation gas to detect an inhalation pressure; and sensors configured to determine measured values for determining a compliance of lungs of the patient being ventilated by means of the ventilator, the determined compliance being provided as output for determining the pressure target value during the phase of exhalation.

* * * * *